United States Patent
Hsieh et al.

(10) Patent No.: US 8,331,001 B2
(45) Date of Patent: Dec. 11, 2012

(54) WELDING FILTER DEVICE AND CONTROL METHOD THEREOF

(75) Inventors: Chien-Hsing Hsieh, Taoyuan Hsien (TW); Edward Martin, Taunton, MA (US); Chia-Hung Chen, Taoyuan Hsien (TW)

(73) Assignee: Arcmask Optech Co., Ltd., Taoyuan Hsien (TW)

( * ) Notice: Subject to any disclaimer, the term of this patent is extended or adjusted under 35 U.S.C. 154(b) by 161 days.

(21) Appl. No.: 13/040,257

(22) Filed: Mar. 3, 2011

(65) Prior Publication Data

US 2012/0176659 A1 Jul. 12, 2012

(30) Foreign Application Priority Data

Jan. 12, 2011 (CN) .......................... 2011 1 0009635

(51) Int. Cl.
*G02F 1/1335* (2006.01)
*A61F 9/06* (2006.01)
(52) U.S. Cl. .................. 359/14; 349/11; 349/13; 2/8.2; 2/8.3; 2/8.7; 2/8.8; 250/201.1; 250/227.14
(58) Field of Classification Search .................... 349/11, 349/14, 13; 2/8.2–8.8; 250/201.1, 227.14
See application file for complete search history.

(56) References Cited

U.S. PATENT DOCUMENTS

| 6,614,409 | B1 * | 9/2003 | Bae ................................... 345/8 |
| 2007/0056073 | A1 * | 3/2007 | Martin et al. ....................... 2/8.8 |
| 2008/0068521 | A1 * | 3/2008 | Cottier ............................. 349/14 |
| 2010/0140241 | A1 * | 6/2010 | Martin et al. ............. 219/130.21 |

* cited by examiner

*Primary Examiner* — Evelyn A. Lester
(74) *Attorney, Agent, or Firm* — CKC & Partners Co., Ltd.

(57) ABSTRACT

The welding filter device includes a light sensor, a microprocessor, a liquid crystal display, and a user interface. The light sensor senses light to generate a welding signal and a light source intensity signal. The microprocessor comprises a determining module, a control module, a regulating module, and a storage module. The determining module receives the welding signal and determines whether to activate a welding mechanism. The control module receives the light source intensity signal and outputs a control signal. The liquid crystal display presents a first display status according to the control signal. The user interface is used to generate a setting signal; wherein when the liquid crystal display presents the first display status, the regulating module receives the setting signal to regulate the settings so that the liquid crystal display presents a second display status. Furthermore, a method for controlling the welding filter device is also disclosed herein.

10 Claims, 5 Drawing Sheets

WELDING FILTER DEVICE AND CONTROL METHOD THEREOF

RELATED APPLICATIONS

This application claims priority to Chinese Application Serial Number 201110009635.4, filed Jan. 12, 2011, which is herein incorporated by reference.

BACKGROUND

1. Field of Invention

The embodiment of the present invention relates generally to a method of a filter device and, more particularly, to a welding filter device with learning and memorizing function.

2. Description of Related Art

Recent years, demands for more convenient, robust and economical goods continue to rise with the advancement and progress of industry and social-economic. As such, products with more economic values are being developed to meet these and other needs.

Electric welding is commonly used to connect two metal pieces. Generally, the surfaces of the two metal pieces are heated to melt, and then the metal pieces are jointed together. However, during this high-temperature welding process, welding sparks and sputtered solders and metal shreds would be resulted from the molten metal. As such, welding masks are required to protect the eyes and face from the sparks and the sputtered solders and shreds, according to safety protocols.

Conventional welding masks can only provide one single shade level, and they cannot be adjusted to provide different shade, levels pursuant to consumer's needs. As such, they are not suitable for use in wide varieties of welds and different intensities. Also, in addition to eye-shading capability, a well-designed welding helmet should be able to provide extra functions that may be adjusted depending on welding applications. Hence, a more flexible, multi-function welding helmet is highly anticipated.

In view of the above, the existing welding helmet still has obvious inconvenience and defects and needs further improvement. In order to solve the above problems, those skilled in the art are trying hard to find a solution, but no applicable method is put forward. Therefore, it is an important subject and also a purpose in need of improvement that how to provide different kinds of dark states for a user based on the different welding condition and provide the user a proper setting in any welding condition to satisfy the demand of the user.

SUMMARY

A welding filter device is provided so as to provide different kinds of dark states for a user based on the different welding condition; and further, the welding filter device can provide the user a proper setting in any welding condition to satisfy the demand of the user.

Thus, one aspect of the embodiment of the present invention is to provide a welding filter device. The welding filter device comprises a light sensor, a microprocessor, a liquid crystal display, and a user interface. The light sensor senses light to generate a welding signal and a light source intensity signal.

In addition, the microprocessor comprises a determining module, control module, a regulating module, and a storage module. The determining module is electrically connected to the light sensor for receiving the welding signal and determining whether to activate a welding mechanism. The control module is electrically connected to the light sensor, wherein when the welding mechanism is activated, the control module receives the light source intensity signal and outputs a control signal according to the light source intensity signal. The regulating module is electrically connected to the control module. The storage module is electrically connected to the control module.

Furthermore, the liquid crystal display controls at least one setting of the liquid crystal display according to the control signal to present a first display status. The user interface is electrically connected to the regulating module for generating a setting signal; wherein when the liquid crystal display presents the first display status, the regulating module receives the setting signal to regulate the setting of the liquid crystal display so that the liquid crystal display presents a second display status.

Moreover, the storage module stores the second display status of the liquid crystal display based on different kinds of light so that next time the welding filter device is used, when the light sensor senses the light, the control module outputs the control signal according to the second display status stored in the storage module for controlling the liquid crystal display to present the second display status.

In one embodiment of the present invention, the light sensor is a photodiode, a photoresistor, a solar panel, or a phototransistor.

In another embodiment of the present invention, the welding filter device further comprises a solar panel. The solar panel is electrically connected to the microprocessor for receiving the light and transducing the light into electrical energy so that the solar panel is used as a power auxiliary device.

In yet another embodiment of the present invention, the welding filter device further comprises a display device. The display device is electrically connected to the control module for displaying the setting according to the control signal.

In still another embodiment of the present invention, the welding filter device further comprises an amplifier. The amplifier is electrically connected to the light sensor and the control module for amplifying the light source intensity signal.

In another aspect, the embodiment of the present invention provides a method for controlling a welding filter device. The method comprises the steps of sensing light for generating a welding signal; receiving the welding signal and determining whether to activate a welding mechanism; if it's determined that the welding mechanism is activated, sensing the light for generating a light source intensity signal; outputting a control signal according to the light source intensity signal; controlling at least one setting of a liquid crystal display according to the control signal so that the liquid crystal display presents a first display status; generating a setting signal when the liquid crystal display presents the first display status; regulating the setting of the liquid crystal display so that the liquid crystal display presents a second display status; and storing the second display status of the liquid crystal display based on different kinds of light so that next time the welding filter device is used, when the light sensor senses the light, the control signal is outputted according to the second display status for controlling the liquid crystal display to present the second display status.

In one embodiment of the present invention, the step of sensing the light is performed with at least one light sensor.

In another embodiment of the present invention, the light sensor is a photodiode, a photoresistor, a solar panel, or a phototransistor.

In yet another embodiment of the present invention, the step of generating the setting signal is performed with a user interface, the user interface is used to generate the setting signal.

In still another embodiment of the present invention, the step of storing the second display status of the liquid crystal display based on different kinds of light is performed with a storage module.

As a result, the embodiment of the present invention provides a welding filter device so as to provide different kinds of shades for a user based on the different welding condition; and further, the welding filter device can provide the user a proper setting in any welding condition to satisfy the demand of the user.

It is to be understood that both the foregoing general description and the following detailed description are by examples, and are intended to provide further explanation of the invention as claimed.

BRIEF DESCRIPTION OF THE DRAWINGS

The invention can be more fully understood by reading the detailed description of the embodiments, with reference made to the accompanying drawings as follows.

DETAILED DESCRIPTION

The present disclosure is more particularly described in the following examples that are intended as illustrative only since numerous modifications and variations therein will be apparent to those skilled in the art. Various embodiments of the disclosure are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. The use of examples anywhere in this specification, including examples of any terms discussed herein, is illustrative only, and in no way limits the scope and meaning of the disclosure or of any exemplified term. Likewise, the disclosure is not limited to various embodiments given in this specification.

As used herein, "around", "about" or "approximately" shall generally mean within 20 percent, preferably within 10 percent, and more preferably within 5 percent of a given, value or range. Numerical quantities given herein are approximate, meaning that the term "around", "about" or "approximately" can be inferred if not expressly stated.

As used herein, the terms "comprising," "including," "having," "containing," "involving," and the like are to be understood to be open-ended, i.e., to mean including but not limited to.

Figure 1:
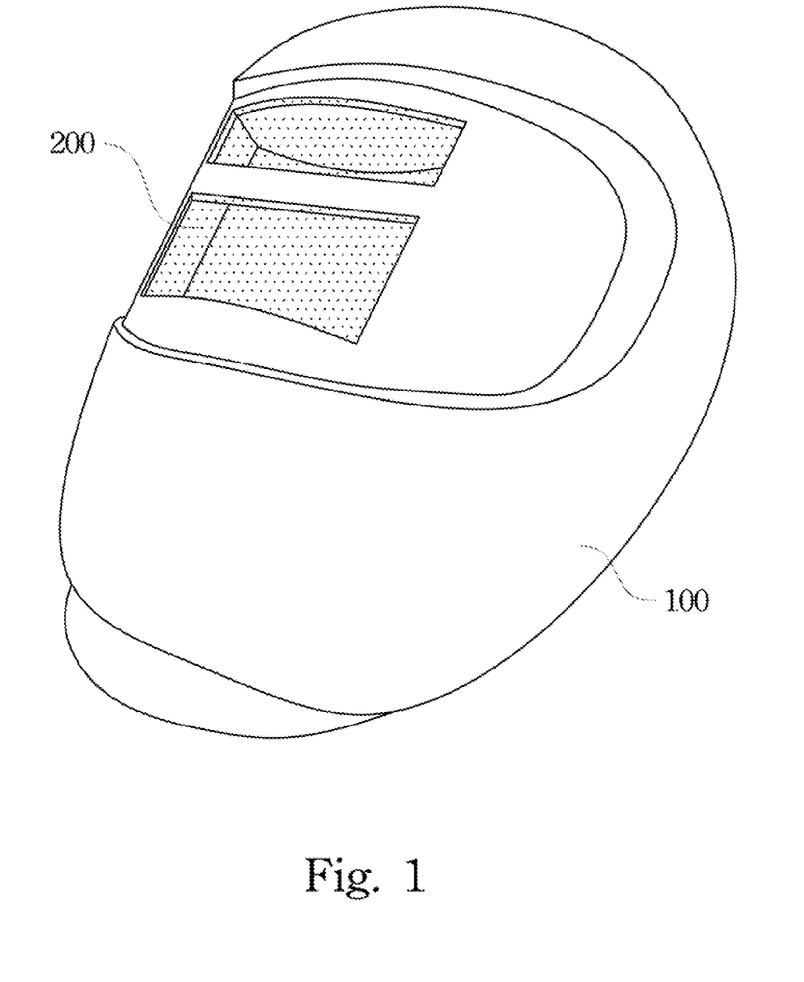
FIG. 1 shows schematically a diagram of a welding mask with a welding filter device according to one embodiment of the present invention.

FIG. 1 shows schematically a diagram of a welding mask 100 with a welding filter device 200 according to one embodiment of the present invention. As shown in FIG. 1, the welding mask 100 is schematically shown, and the welding mask 100 has a welding filter device 200 of one embodiment of the present invention to prevent a user from danger during a welding work. However, the shape of the welding mask 100 merely exemplifies the embodiment of the present invention but not limited to, those with ordinary skill in the art could make numerous alterations to the disclosed embodiments without departing from the spirit or scope of this invention to prevent the user from danger during the welding work.

Figure 2A:
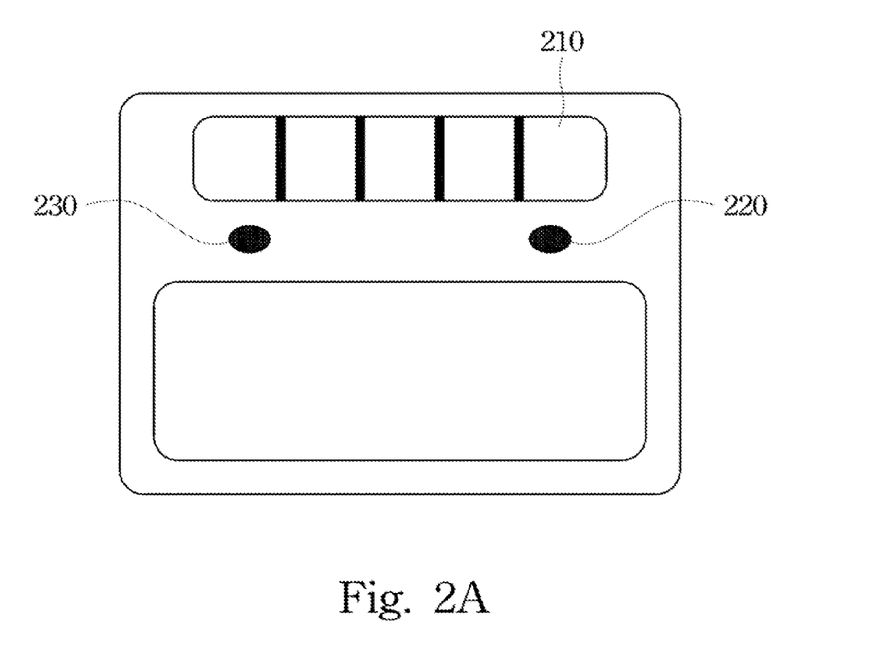
FIG. 2A shows schematically a front view of the welding filter device according to another embodiment of the present invention.

FIG. 2A shows schematically a front view of the welding filter device according to another embodiment of the present invention. As shown in FIG. 2A, the front of the welding filter device 200 can comprise a solar panel 210, a first light sensor 220, and a second light sensor 230.

Figure 2B:
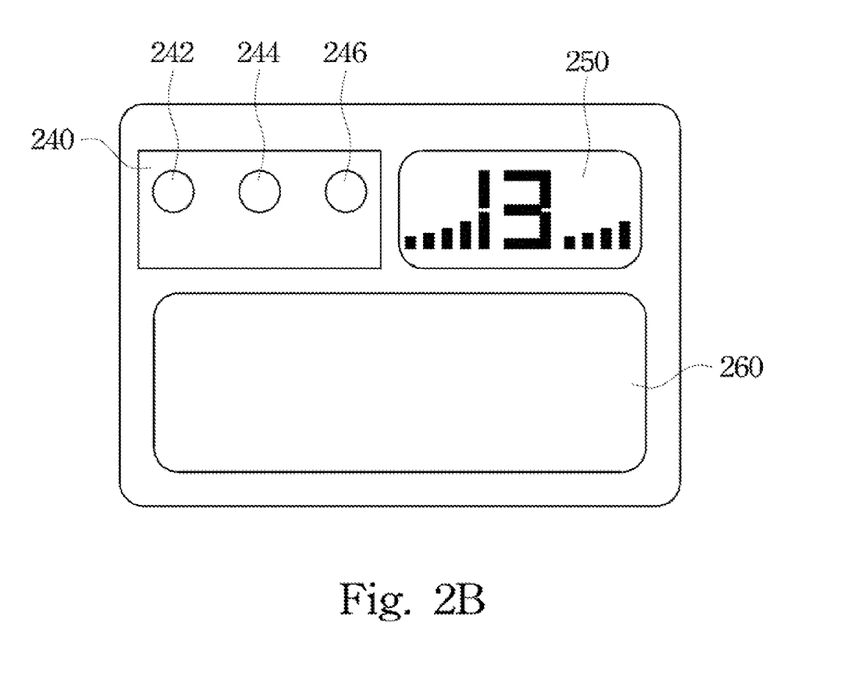
FIG. 2B shows schematically a back view of the welding filter device according to another embodiment of the present invention.

FIG. 2B shows schematically a back view of the welding filter device according to another embodiment of the present invention. As shown in FIG. 2B, the back of the welding filter device 200 can comprise a user interface 240, a display device 250, and a liquid crystal display 260. The above mentioned embodiment is merely exemplary of the invention but not limited to, those with ordinary skill in the art could selectively dispose the elements in the welding filter device 200 with actual demand.

In one embodiment, the first light sensor 220 can be any element which can transduce light into a electrical signal, for example, a photodiode, photoresistor, solar panel, or phototransistor. The first light sensor 220 mainly receives the light generated from the welding work and provides the signal corresponding to the light to the microprocessor 280 so that the microprocessor 280 can determine whether there is a welding signal.

In addition, the second light sensor 230 can also be any element which can transduce light into a electrical signal, for example, a photodiode, photoresistor, solar panel, or phototransistor. The second light sensor 230 also receives the light generated form the welding work, but the signal the second light sensor 230 provides to the microprocessor 280 is a light source intensity signal so that the microprocessor 280 can determine the light source intensity according to the light source intensity signal, and the microprocessor 280 can set the dark state and relative setting of the welding filter device 200.

Reference is now made to FIG. 2A and FIG. 2B, the solar panel 210 is a device to provide the welding filter device 200 an, auxiliary power during the welding work. The above mentioned embodiment is exemplary of the invention but not limited to those with ordinary skill in the art know that embodiment of the invention can work properly without the solar panel 210.

In practical, the user interface 240 can comprise a shade select switch 242, a sensitivity select switch 244, and a delay time select switch 246 for the user to select the work condition of the welding filter device 200 they need.

In an optional embodiment, the display device 250 is used to present the setting values of the liquid crystal display 260 according to the settings the user inputs by the user interface 240.

In one embodiment, the liquid crystal display 260 can regulate the shade of the liquid crystal display 260 according to an AC square wave. For instance, the liquid crystal display 260 will present light state when the liquid crystal display 260 does not receive any voltage, and the liquid crystal display 260 will present dark state when the liquid crystal display 260 receives the voltage. The welding filter device 200 can be performed with a microprocessor 280, and the working mechanism of the embodiment in present invention will be shown below.

Figure 3:
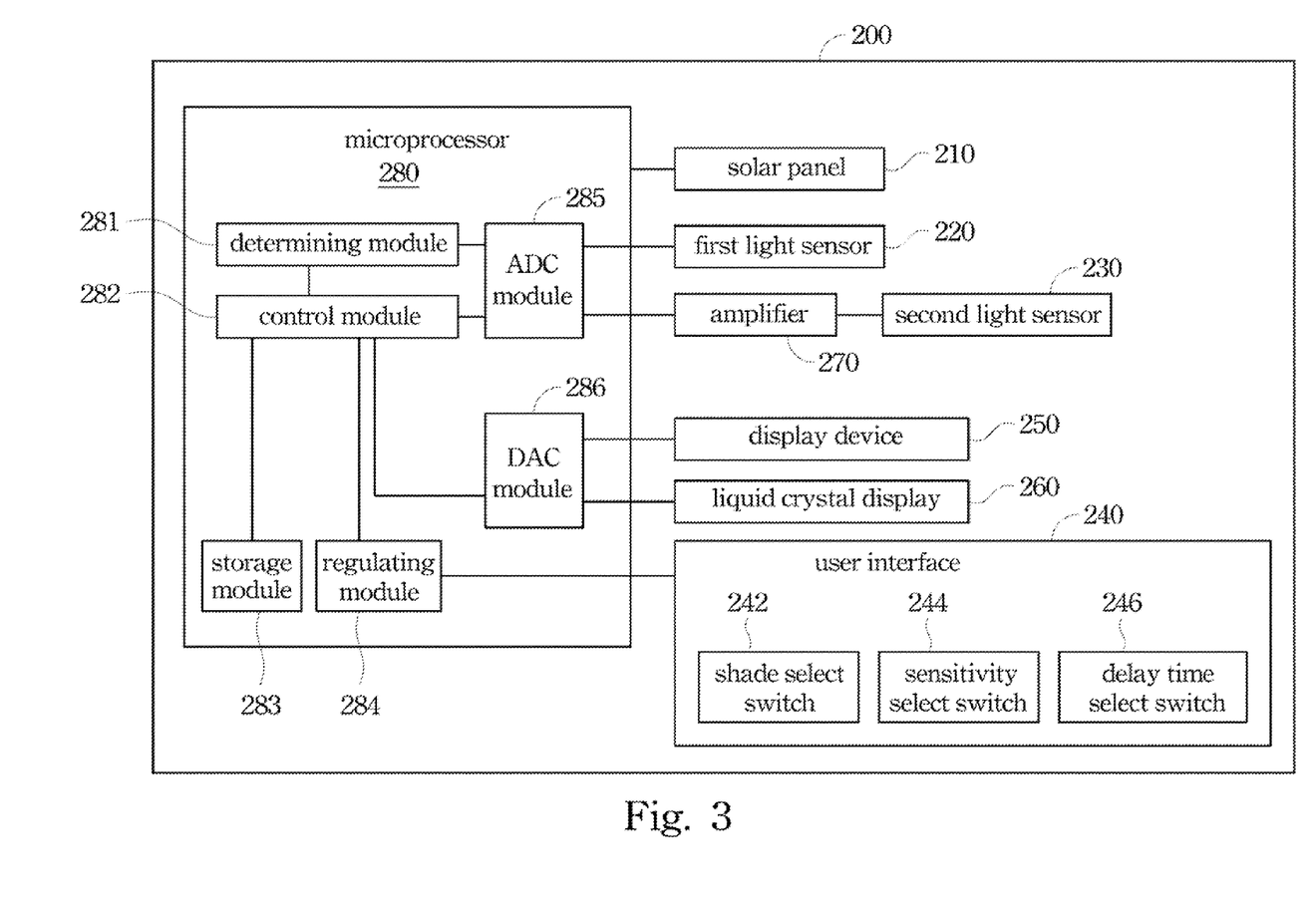
FIG. 3 shows schematically a block diagram of the welding filter device according to yet another embodiment of the present invention.
Figure 4:
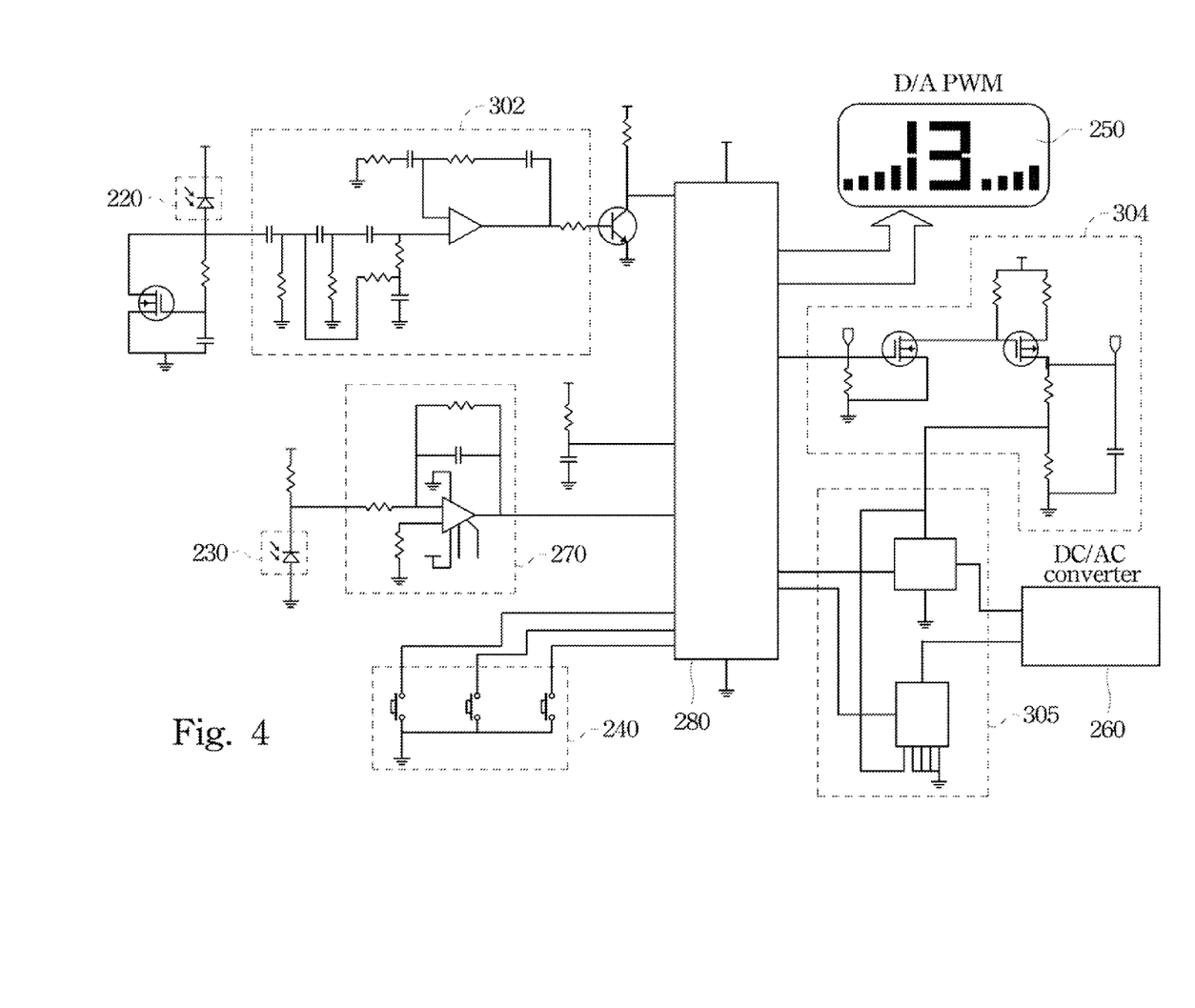
FIG. 4 shows schematically a circuit block diagram of the welding filter device according to still another embodiment of the present invention.

FIG. 3 shows schematically a block diagram of the welding filter device 200 according to yet another embodiment of the present invention. FIG. 4 shows schematically a circuit block diagram of the welding filter device 200 according to still another embodiment of the present invention.

Reference is now made to FIGS. 3 and 4, the welding filter device 200 comprise a first light sensor 220, a second light sensor 230, a microprocessor 280, a liquid crystal display 260, and a user interface 240.

In practical, the first light sensor 220 senses light to generate a welding signal. The second light sensor 230 senses the light to generate a light source intensity signal. Correspondingly, the microprocessor 280 comprises a determining module 281, and a control module 282. The determining module 281 is electrically connected to the first light sensor 220 and receives the is welding signal generated from the first light sensor 220 for determining whether to activate a welding mechanism.

Particularly, reference is now made to FIG. 4. The first light sensor 220 senses the light generated from the welding work and transduces the light into current signal when the welding work starts. The current signal will be transduced into welding signal by the high-pass filter 302. When the welding work starts, the welding signal generated from the welding work is a low level signal; at this time, the determining module 281 of the microprocessor 280 will determine that the welding mechanism is started, and the liquid crystal display 260 will be controlled to present a dark state.

In one embodiment, the solar panel 210 is electrically connected to the microprocessor 280 and transduces light generated from welding work into electrical energy as a power auxiliary device of the welding filter device 200. The above mentioned embodiment is exemplary of the invention but not limited to, those with ordinary skill in the art know that embodiment of the invention can work properly without the solar panel 210.

In addition, the control module 282 is electrically connected to the second light sensor 230, wherein when the determining module 281 determines that the welding mechanism is activated; the control module source intensity signal generated by the second light sensor 230 and outputs a control signal according to the light source intensity signal.

In one embodiment, the welding filter device 200 further comprises an amplifier 270. The amplifier 270 is electrically connected to the second light sensor 230 and the control module 282 for amplifying the light source intensity signal.

Particularly, as shown in FIG. 4, when the determining module 281 determines that the welding mechanism is activated, the control module 282 receives the light source intensity signal generated by the second light sensor 230. The light source intensity signal is generated form a photoelectric conversion by the second light sensor 230, wherein the photoelectric conversion is that the second light sensor 230 senses the light generated from welding work and transduces the light into the light source intensity signal. Then, the light source intensity signal can be amplified by the amplifier 270 and provide to the microprocessor 280.

In another embodiment, the microprocessor 280 further comprises an ADC module 285. The ADC module 285 is electrically connected to the first light sensor 220, the second light sensor 230, and the control module 282. The ADC module 285 is used to perform an analog to digital conversion to the welding signal and the light source intensity signal and converts the welding signal and the light source intensity signal from an analog signal to a digital signal; then, the welding signal and the light source intensity signal will be provided to the control module 282.

Furthermore, the microprocessor 280 further comprises a DAC module 286. The DAC module 286 is electrically connected to the display device 250, the liquid crystal display 260, and the control module 282. The DAC module 286 is used to perform a digital to analog conversion to the control signal and converts the control signal from a digital signal to an analog signal; then, the control signal will be provided to the display device 250 and the liquid crystal display 260.

As shown in FIG. 4, the welding filter device 200 comprises a D/A PWM 304. The D/A PWM 304 is mainly used to provide a voltage for the welding filter device 200 to change the shade thereof. The voltage converted by the D/A PWM 304 is a shade voltage.

Moreover, the welding filter device 200 can comprise a DC/AC converter 305. The shade voltage can be converted by the DC/AC converter 305 to generate a control signal, wherein the control signal is a voltage signal. The control signal can be provided to the liquid crystal display 260 so that the liquid crystal display 260 can regulate the transmittance of itself based on the voltage, for example, the bigger the voltage is, the lower the transmittance will be.

In an optional embodiment, the microprocessor 280 can comprise a storage module 283. The storage module 283 is electrically connected to the control module 282. It is noteworthy that the storage module 283 has an initial light intensity and the control signal table stored therein, and when the welding filter device 200 is used in a different welding condition for the first time the microprocessor 280 would receive a signal representing the light source intensity signal and lookup in the initial light intensity and the control signal table to find a control signal corresponding to the light source intensity signal. Thereafter, the microprocessor 280 would output the control signal.

Next, the liquid crystal display 260 is operable to control its shade, sensitivity, and delay time based on the control signal to present the first display status. The first display status is the display status of the liquid crystal display 260 set by the welding filter device 200 under the initial status.

In the present embodiment, the microprocessor 280 further comprises a regulating module 284. The regulating module 284 is electrically connected to the control module 282, and the user interface 240 is electrically connected to the regulating module 284. The user interface 240 comprises a shade select switch 242, a sensitivity select switch 244, and a delay time select switch 246. The shade select switch 242 is operable to generate a shade regulating signal, the sensitivity select switch 244 is operable to generate a sensitivity regulating signal, and the delay time select switch 246 is operable to generate a delay time regulating signal.

According to the principles and spirits of the present invention, the regulating module 284 is configured to receive the shade regulating signal, the sensitivity regulating signal, and the delay time regulating signal when, the liquid crystal display 260 presents the first display status (i.e., the initial status), so as to regulate the shade, the sensitivity, and the delay time of the liquid crystal is display such that the liquid crystal display 260 may present a second display status.

To sum up, the present embodiment(s) is directed to welding filter devices and methods for controlling the same. Specifically, after the welding filter device 200 detects the electric welding light and presents the first display status (initial status), users may select the desired shade level and other settings via the buttons of the user interface (such as the user interface 240 of FIG. 4) depending on their preferences. Then, these settings are provided to the microprocessor 280 so that the liquid crystal display 260 is operable to present the second display status which is the display status of the liquid crystal display 260 preferred by the users.

Reference is now made to both FIG. 3 and FIG. 4. In an optional embodiment, the welding filter device 200 further comprises a display device 250. The display device 250 is electrically connected to the control module 282 and operable to show the shade, the sensitivity and the delay time based on the control signal so that the user may be aware of the various settings of the liquid crystal display 260. In the present embodiment, the microprocessor 280 comprises a storage module 283 that is used to store the second display status (the regulated status) present by the liquid crystal display 260 under various light. As such when the second light sensor 230 senses the light, the control module 282 would output the control signal based on the second display status corresponding to the light intensity stored in the store module 283 so as to control the liquid crystal display 260 to present the second display status.

Specifically, since the microprocessor 280 comprises the storage module 283, the welding filter device 200 may use the storage module 283 to store the shade and the settings preferred by the user under various light intensities after the liquid crystal display 260 has been set by the user pursuant to this/her preferences to present the second display status.

As such, if light with the similar intensity is generated during the following welding operation under the same operation conditions, the welding filter device 200 is operable to provide the preferred setting(s) based on the said light intensity so as to, automatically regulate the shade and settings of the liquid crystal display 260 so that the liquid crystal display 260 presents the second display status.

In view of the foregoing, the present welding filter device 200 is equipped with learning and memorizing, function so that the welding filter device 200 is operable to memorize the user's preferences under different operation conditions and present these preferences in the subsequent use of this device.

As such, after several times of operation and learning/memorizing process, the welding filter device 200 would become the exclusive adaptation of the user so that the welding filter device 200 is able to automatically regulate the shade and various settings in accordance with different welding conditions so that the liquid crystal display 260 is operable to present the second display status without any manual regulation from the user.

Figure 5:
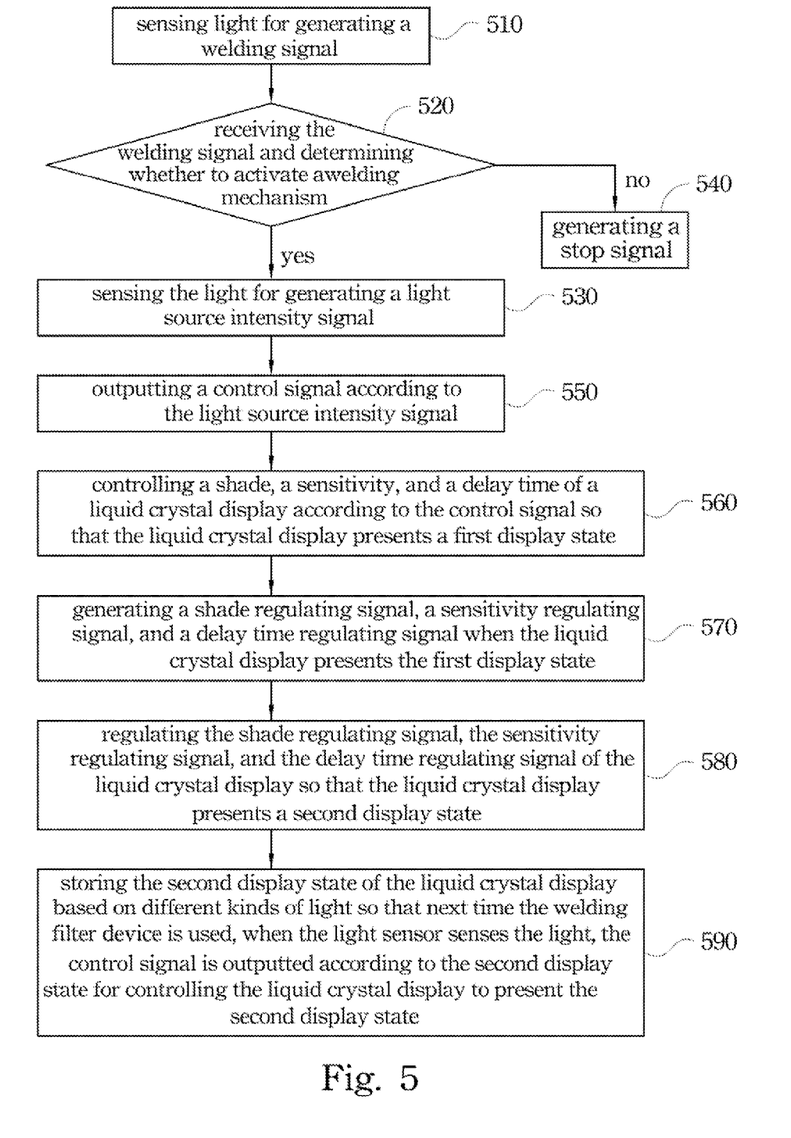
FIG. 5 shows schematically a flow diagram of a method for controlling the welding filter device according to yet another embodiment of the present invention.

FIG. 5 shows schematically a flow diagram of a method for controlling the welding filter device 200 according to yet another embodiment of the present invention.

As shown in FIG. 5, the method for controlling the welding filter device 200 comprises the step of sensing light for generating a, welding signal (step 510).

The step 510 can be illustrated with FIG. 1. The step of sensing the light can be performed with the first light sensor to generate a welding signal. In the embodiment, the first light sensor 220 can be any device which can transduce light into electric signal such as photodiode, phototransistor, and so on.

After generating the welding signal, the method comprises receiving the welding signal and determining whether to activate a welding mechanism (step 520).

In step 520, the step of receiving the welding signal and determining whether to activate a welding mechanism can be performed by the determining module 281 of the microprocessor 280.

If it's determining that the welding mechanism is activated, the method comprises sensing the light for generating a light source intensity signal (step 530). In this step, the second light sensor 230 can be used to sense the light for generating the light source intensity signal. Similarly, the second light sensor 230 can also be any device which can transduce light into electric signal such as photodiode, phototransistor, solar panel, phototransistor, and so on. If it's determined that the welding mechanism isn't activated, the method comprises generating a stop signal (step 540).

Then, the method comprises outputting a control signal according to the light source intensity signal (step 550). In the step, the step of outputting a control signal according to the light source intensity signal can be performed with the control module 282 of the microprocessor 280.

After that, the method comprises controlling at least one setting of a liquid crystal display 260 according to the control signal so that the liquid crystal display 260 presents a first display status (step 560). The foregoing at least one setting can be a shade, a sensitivity, a delay time, and so on.

When the liquid crystal display presents the first display status, the method comprises generating a setting signal (step 570).

In one embodiment, the step 570 can be performed with the user interface 240, and the user interface 240 generates the setting signal.

Furthermore, the method comprises regulating the setting of the liquid crystal display according to setting signal so that the liquid crystal display presents a second display status (step 580).

According to the principles and spirit of the present invention, in step 580, the regulating module 284 of the microprocessor 280 receives the setting signal when the liquid crystal display 260 presents the first display status (initial condition) to regulate the setting of the liquid crystal display 260 such as a shade, a sensitivity, a delay time, and so on, so that the liquid crystal display 260 presents a second display status.

After the liquid crystal display 260 presents the second display status, the method comprises storing the second display status presented by the liquid crystal display 260 in different light. Next time the welding filter device 200 senses light, the welding filter device 200 outputs the control signal according to the second display status the light corresponding to so that the liquid crystal display 260 can be controlled to present the second display status (step 590).

In an optional embodiment, the step of storing the second display status presented by the liquid crystal display 260 in different light is performed with the storage module 283 of the microprocessor 280.

Particularly, the user can regulate the setting of the liquid crystal display 260 according to the demand of the user and present the second display status due to the storage module 283 of the microprocessor 280; then, the welding filter device 200 can use the storage module 283 to store the shade and the settings according to the demand of the user.

Therefore, the method for controlling the welding filter device 200 can be used to acquire the setting the user stores accurately according to the light intensity when the welding filter device 200 receives the same light intensity in the same condition of the welding work; then, the shade and the settings of the liquid crystal display 260 can be automatically regulated so that the liquid crystal display 260 presents the second display status.

As a result, the welding filter device 200 controlled by the foregoing method can be an exclusive device for the user after several learning and memorizing operations. The welding filter device 200 can automatically regulate the shade and the settings according to different welding conditions without any manual regulation form the user such that the liquid crystal display 260 presents the second display status.

Those having skill in the art will appreciate that the method for controlling the welding filter device 200 can be performed with software, hardware, and/or firmware. For example, if an implementer determines that speed and accuracy are paramount, the implementer may opt for a mainly hardware and/or firmware implementation; alternatively, if flexibility is paramount, the implementer may opt for a mainly software implementation; or, yet again alternatively, the implementer may opt for some combination of hardware, software, and/or firmware. Those skilled in will recognize that optical aspects of implementations will typically employ optically oriented hardware, software, and or firmware.

In addition, those skilled in the art will appreciate that each of the steps of the method for controlling the welding filter device 200 named after the function thereof is merely used to describe the technology in the embodiment of the present invention in detail but not limited to. Therefore, combining the steps of said method into one step, dividing the steps into several steps, or rearranging the order of the steps is within the scope of the embodiment in the present invention.

In view of the foregoing embodiments of the present invention, many advantages of the present invention are now apparent. The embodiment of the present invention provides a welding filter device so as to provide different kinds of shades for a user based on the different welding condition; and further, the welding filter device can provide the user a proper setting in any welding condition to satisfy the demand of the user. Furthermore, the welding filter device 200 controlled by the foregoing method can be an exclusive device for the user after several learning and memorizing operations. The welding filter device 200 can automatically regulate the shade and the settings according to different welding conditions without any manual regulation form the user such that the liquid crystal display 260 presents the display status preferred by the user.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention, and the scope thereof is determined by the claims that follow.

What is claimed is:

1. A welding filter device, comprising:
   a light sensor for sensing light to generate a welding signal and a light source intensity signal;
   a microprocessor, comprising:
   a determining module electrically connected to the light sensor for receiving the welding signal and determining whether to activate a welding mechanism;
   a control module electrically connected to the light sensor, wherein when the welding mechanism is activated, the control module receives the light source intensity signal and outputs a control signal according to the light source intensity signal;
   a regulating module electrically connected to the control module; and
   a storage module electrically connected to the control module;
   a liquid crystal display for controlling at least one setting of the liquid crystal display according to the control signal to present a first display status; and
   a user interface electrically connected to the regulating module for generating a setting signal;
   wherein when the liquid crystal display presents the first display status, the regulating module receives the setting signal to regulate the setting of the liquid crystal display so that the liquid crystal display presents a second display status;
   wherein the storage module stores the second display status of the liquid crystal display based on different kinds of light so that next time the welding filter device is used, when the light sensor senses the light, the control module outputs the control signal according to the second display status stored in the storage module for controlling the liquid crystal display to present the second display status.

2. The welding filter device according to claim 1, wherein the light sensor is a photodiode, a photoresistor, a solar panel, or a phototransistor.

3. The welding filter device according to claim 1, further comprising:
   a solar panel electrically connected to the microprocessor for receiving the light and transducing the light into electrical energy so that the solar panel is used as a power auxiliary device.

4. The welding filter device according to claim 1, further comprising:
   a display device electrically connected to the control module for displaying the setting according to the control signal.

5. The welding filter device according to claim 1, further comprising:
   an amplifier electrically connected to the light sensor and the control module for amplifying the light source intensity signal.

6. A method for controlling a welding filter device, comprising the steps of:
   sensing light for generating a welding signal;
   receiving the welding signal and determining whether to activate a in welding mechanism;
   if it's determined that the welding mechanism is activated, sensing the light for generating a light source intensity signal;
   outputting a control signal according to the light source intensity signal;
   controlling at least one setting of a liquid crystal display according to the control signal so that the liquid crystal display presents a first display status;
   generating a setting signal when the liquid crystal display presents the first display status;
   regulating the setting of the liquid crystal display so that the liquid crystal display presents a second display status; and storing the second display status of the liquid crystal display based on different kinds of light so that next time the welding filter device is used, when the light sensor senses the light, the control signal is outputted according to the second display status for controlling the liquid crystal display to present the second display status.

7. A control method according to claim 6, wherein the step of sensing the light is performed with at least one light sensor.

8. A control method according to claim 7, wherein the light sensor is a photodiode, a photoresistor, a solar panel, or a phototransistor.

9. A control method according to claim 6, wherein the step of generating the setting signal is performed with interface is used to generate the setting signal.

10. A control method according to claim 6, wherein the step of storing the second display status of the liquid crystal display based on different kinds of light is performed with a storage module.

* * * * *